(12) United States Patent
Welch et al.

(10) Patent No.: US 7,385,698 B1
(45) Date of Patent: Jun. 10, 2008

(54) SYSTEM AND METHOD OF SELECTIVELY MONITORING SAMPLE FRONT AND BACKSIDE REFLECTIONS IN ELLIPSOMETER AND THE LIKE SYSTEMS

(75) Inventors: James D. Welch, Omaha, NE (US); John A. Woollam, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 366 days.

(21) Appl. No.: 11/288,785

(22) Filed: Nov. 30, 2005

Related U.S. Application Data

(63) Continuation-in-part of application No. 11/098,669, filed on Apr. 2, 2005, now Pat. No. 7,239,391, which is a continuation-in-part of application No. 10/238,241, filed on Sep. 10, 2002, now Pat. No. 6,937,341, which is a continuation-in-part of application No. 09/756,515, filed on Jan. 9, 2001, now Pat. No. 6,455,853, which is a continuation-in-part of application No. 10/194,881, filed on Jul. 15, 2002, now Pat. No. 6,940,595, which is a continuation-in-part of application No. 09/916,836, filed on Jul. 27, 2001, now Pat. No. 6,636,309.

(60) Provisional application No. 60/639,097, filed on Dec. 27, 2004.

(51) Int. Cl.
  *G01J 4/00* (2006.01)
(52) U.S. Cl. .......................... 356/369; 356/364; 356/365
(58) Field of Classification Search .......... 356/364–369
  See application file for complete search history.

(56) References Cited

U.S. PATENT DOCUMENTS

| 3,799,679 | A  |   | 3/1974  | Simko ........................ 356/200   |
| 5,706,212 | A  | * | 1/1998  | Thompson et al. .......... 356/368       |
| 5,936,734 | A  | * | 8/1999  | Johs et al. ................... 356/364   |
| 6,088,092 | A  |   | 7/2000  | Chen et al. ................ 356/237.2    |
| 6,088,104 | A  |   | 7/2000  | Peterson .................... 356/371     |
| 6,097,482 | A  |   | 8/2000  | Smith et al. ............... 356/237.1    |
| 6,130,749 | A  |   | 10/2000 | Meeks et al. ................ 356/381     |
| 6,166,808 | A  |   | 12/2000 | Greve ........................ 356/375    |
| 6,198,533 | B1 |   | 3/2001  | Meeks et al. ................ 356/381     |
| 6,392,749 | B1 |   | 5/2002  | Meeks et al. ................ 356/381     |
| 6,535,286 | B1 | * | 3/2003  | Green et al. ................ 356/369     |
| 2002/0113200 | A1 |  | 8/2002  | Hajjar et al.                            |

* cited by examiner

*Primary Examiner*—L. G. Lauchman
*Assistant Examiner*—Iyabo S Alli
(74) *Attorney, Agent, or Firm*—James D. Welch

(57) ABSTRACT

A spectrophotometer, reflectometer, ellipsometer polarimeter or the like system having a detector means for independently intercepting electromagnetic radiation reflected from a sample frontside or backside, and methodology for pursuing less correlated determination of refractive index and thickness values.

20 Claims, 4 Drawing Sheets

SYSTEM AND METHOD OF SELECTIVELY MONITORING SAMPLE FRONT AND BACKSIDE REFLECTIONS IN ELLIPSOMETER AND THE LIKE SYSTEMS

This application is a CIP of application Ser. No. 11/098,669 Filed Apr. 2, 2005 now U.S. Pat. No. 7,239,391 and therevia of Ser. No. 10/238,241 Filed Sep. 10, 2002 now U.S. Pat. No. 6,937,341 and therevia of Ser. No. 09/756,515 Filed Jan. 9, 2001, (U.S. Pat. No. 6,455,853). Further this application is a CIP of Ser. No. 10/194,881 Filed Jul. 15, 2002 now U.S. Pat. No. 6,940,595 and therevia of Ser. No. 09/916,836 Filed Jul. 27, 2001, (now U.S. Pat. No. 6,636,309). This application also claims Benefit of Provisional Application Ser. No. 60/639,097 Filed Dec. 27, 2004.

TECHNICAL AREA

The disclosed invention relates to systems and methods of monitoring electromagnetic radiation reflected from a sample, and more particularly to a spectrophotometer, reflectometer, ellipsometer, polarimeter or the like system comprising means for selectively independently intercepting only components thereof reflected from the front or only from the backside of said sample, and further comprising methodology for pursuing determination of less correlated refractive index and thickness using data from a single sample.

BACKGROUND

A problem inherent in monitoring electromagnetic radiation which is reflected from a sample frontside, is that it often is contaminated with reflections from the backside thereof. One approach to preventing this problem is to roughen the backside. Another is to place a mask on the surface of the sample which allows surface reflections to proceed, but prevents backside reflections from exiting. Said approach is disclosed in patent application Ser. No. 10/731,202 Filed Dec. 10, 2003, with benefit of Provisional 60/452,673 Filed Mar. 10, 2003. Another approach yet is to place a blocking means between the sample and the detector which blocks backside reflections but lets front surface reflections proceed into the detector. Said approaches, however, do not allow for selectively monitoring electromagnetic radiation reflected from the front or backside. In that light it is noted that backside reflected electromagnetic energy contains information which is different from that contained in frontside reflections.

Continuing, it is also disclosed that ellipsometry monitors the product of refractive index and thickness in samples investigated thereby, and that said parameters are correlated in what can be termed an optical thickness. A known approach to breaking the correlation is to obtain data from two samples comprising the same material(s) but which samples are of different thicknesses. Simultaneously regression of the data obtained from both sides onto corresponding mathematical models leads to substantially uncorrelated evaluation of refractive index and thicknesses.

It is also mentioned that it is known to obtain data from front and backsides of a sample and simultaneously regress said data onto a mathematical model therefore.

Known Patents and Published Applications are:

Patent Application No. 2002/0113200 A1 was identified as an aperture 103A is disclosed which can be placed near a detector to block entry of one of two beams from different sources.

U.S. Pat. No. 3,799,679 to Simko is disclosed as an iris (38) is present near a detector which can be adjusted to block entry of backside reflection thereinto.

Patents to Meeks, U.S. Pat. Nos. 6,130,749, 6,198,533 and 6,392,749 are disclosed for the presence of a hole 2022 in an integrating sphere near, but not atop a sample.

U.S. Pat. No. 6,088,092 to Chen et al. is disclosed as it applies a spatial filter (28) to block backside reflection entry into a detector.

U.S. Pat. No. 6,088,104 to Peterson is disclosed as a blocking element (B) is present which can be used to block electromagnetic radiation entry to a detector.

U.S. Pat. No. 6,097,482 to Smith et al. is disclosed as it applies baffles to block light entry to a detector.

U.S. Pat. No. 6,166,808 to Greve is disclosed as it describes use of an aperture near a detector to block backside reflections entry to a detector.

U.S. Pat. No. 5,936,734 is identified as it describes a method of partitioning electromagnetic radiation into coherent and incoherent portions when calculating intensity.

U.S. Pat. No. 6,455,853 to Herzinger at al. is identified as it describes obtaining data from both sides of a sample.

Need remains for a system and method of intercepting only desired portions, such as only electromagnetic radiation reflected from a sample surface or from its backside, and for methodology which facilitates breaking of correlation between refractive index and thickness, using a single sample.

DISCLOSURE OF THE INVENTION

Where an electromagnetic beam is focused onto a sample, it occurs that frontside and backside reflections are spatially separated more than is the case where a beam is not focused. Particularly, but not exclusively, in the case where a beam is focused onto a sample by a converging lens, the present invention teaches that a convenient approach to avoiding complications associated with backside reflections entering a detector along with surface reflections, is to utilize a physically small size detector, or a light fiber which leads to a detector, and move it such that only an intended frontside reflection is intercepted. Said method can also be beneficial in that it allows monitoring only backside reflections as well. In use the detector or optical fiber can be moved to locate peaks in intensity which correspond to primarily frontside or backside reflections, and once located, data can be acquired from received electromagnetic radiation.

The disclosed invention then comprises a system which presents as a sequential combination of a source of electromagnetic radiation, a sample having front and backsides, and a detector; said source, sample and detector being oriented such that electromagnetic radiation from said source is directed at said sample at an oblique angle, reflects therefrom and enters said detector. The detector is of a small dimension as compared to the spread between sample frontside and sample backside reflections at the location thereof or said detector is mounted to allow movement into electromagnetic radiation reflected from the frontside or backside. Said system can further comprise at least one selection from the group consisting of:

a polarizer means between said source and sample;
an analyzer means between said sample and detector;
a compensator between said source and detector; and
at least one focusing lens positioned such that electromagnetic radiation from said source is directed at said sample at an oblique angle;

and in which said system is an ellipsometer or polarimeter.

Another recitation of the present invention system provides that it is sequentially comprised of a source of electromagnetic radiation, a sample having front and a backsides, and an optical fiber and detector. Said source, sample and optical fiber are oriented such that electromagnetic radiation from said source is directed at said sample at an oblique angle, reflects therefrom and enters said optical fiber. The optical fiber is of a small dimension as compared to the spread between sample frontside and sample backside reflections at the location thereof, and said optical fiber is mounted to allow movement into electromagnetic radiation reflected from the frontside or backside.

Again, the system can further comprise providing at least one selection from the group consisting of:
- a polarizer means between said source and sample;
- an analyzer means between said sample and detector;
- a compensator between said source and detector; and
- at least one focusing lens positioned such that electromagnetic radiation from said source is directed at said sample at an oblique angle;

and in which said system is an ellipsometer or polarimeter.

A method of selectively monitoring frontside or backside reflections from a sample, comprising the steps of:
- a) providing a system which is sequentially comprised of a source of electromagnetic radiation, a sample having front and backsides, and a detector; said source, sample and detector being oriented such that electromagnetic radiation from said source is directed at said sample at an oblique angle, reflects therefrom and enters said detector, said detector being of a small dimension as compared to the spread between sample frontside and sample backside reflections at the location thereof, said detector being mounted to allow movement into electromagnetic radiation reflected from the frontside or backside;
- b) causing a beam of electromagnetic radiation to reflect from said sample; and
- c) moving said detector into electromagnetic radiation reflected from the sample frontside or from the sample backside and obtaining data.

Said method can include, in the step of providing a system, providing at least one selection from the group consisting of:
- a polarizer means between said source and sample;
- an analyzer means between said sample and detector;
- a compensator between said source and detector; and
- at least one focusing lens positioned such that electromagnetic radiation from said source is directed at said sample at an oblique angle;

and in which said system is an ellipsometer or polarimeter.

Another recitation of a method of selectively monitoring frontside or backside reflections from a sample, comprises the steps of:
- a) providing a system which is sequentially comprised of a source of electromagnetic radiation, a sample having front and backsides, and an optical fiber and detector; said source, sample and optical fiber being oriented such that electromagnetic radiation from said source is directed at said sample at an oblique angle, reflects therefrom and enters said optical fiber, said optical fiber being of a small dimension as compared to the spread between sample frontside and sample backside reflections at the location thereof, said optical fiber being mounted to allow movement into electromagnetic radiation reflected from the frontside or backside;
- b) causing a beam of electromagnetic radiation to reflect from said sample; and
- c) moving said optical fiber into electromagnetic radiation reflected from the sample frontside or from the sample backside.

Again, the step of providing a system can further comprise providing at least one selection from the group consisting of:
- a polarizer means between said source and sample;
- an analyzer means between said sample and detector;
- a compensator between said source and detector; and
- at least one focusing lens positioned such that electromagnetic radiation from said source is directed at said sample at an oblique angle;

and in which said system is an ellipsometer or polarimeter.

Another method of selectively monitoring frontside or backside reflections from a sample, comprises the steps of:
- a) providing a system which is sequentially comprised of a source of electromagnetic radiation, a sample having front and backsides, and a detector which comprises a plurality of detector elements; said source, sample and detector being oriented such that electromagnetic radiation from said source is directed at said sample at an oblique angle, reflects therefrom and enters said detector, said detector elements being of a small dimension as compared to the spread between sample frontside and sample backside reflections at the location thereof, such that selective monitoring of specific detector elements allows the monitoring of reflections from the frontside and backside independently;
- b) causing a beam of electromagnetic radiation to reflect from said sample; and
- c) monitoring selected detector elements to independently investigate electromagnetic radiation reflected from the sample surface or from the sample backside.

Methodology in which reflections from the front and back of the sample are analyzed separately provides an approach to breaking correlation of thickness and refractive index as reflections from the surface provide information primarily about refractive index of the surface region of the sample, and reflections from the backside thereof provide information about the bulk of the sample, including refractive index and thickness.

A method of pursuing uncorrelated values for refractive index and thickness of a sample comprising practicing steps a and a' sequentially or simultaneously in either order:
- a) providing a system which is sequentially comprised of a source of electromagnetic radiation, a sample having frontside and a backside, and at least one detector that allows selective monitoring at least two selections from the group consisting of:
  - reflection from the frontside;
  - reflection from the backside; and
  - transmission through the backside;

independently, said detector(s) being selected from the group consisting of:
- comprising a plurality of substantially fixed location detector elements;
- comprising a single movable detector element; and
- comprising a single detector element accessed by a movable optical fiber;

said source, sample and detector being oriented such that electromagnetic radiation from said source is directed at said sample at an oblique angle, reflects therefrom and enters said detector;
- a') providing a mathematical model of said sample;
- b) causing a beam of electromagnetic radiation to impinge onto said sample; and c) independently monitoring at least two selections form the group consisting of:
 reflection from the frontside;
 reflection from the backside; and
 transmission through the backside;
d) simultaneously regressing at least two monitored data sets obtained in step c onto said mathematical model provided in step a'.

Said method can further comprise flipping the sample over so that the sample backside becomes the frontside and the sample frontside becomes the backside, and obtaining data by repeating steps c and d, with the difference being that additional data set(s) are applied in the simultaneous regression in step d.

It is noted that, as the data associated with frontside reflection contains different information than does that associated with the backside reflection and/or transmission, (as it transvered the thickness of the sample), simultaneous regression of the multiple sets of data onto the mathematical model can be expected to, for at least some samples, result in reduced correlation between refractive index and thickness values. Note that said method can involve investigating a sample which comprises a substrate or a substrate and at least one film layer on at least one of the front and backsides thereof. And where a sample comprises one or more films present on the front and/or backside, multiple reflections can be individually intercepted, each of which corresponds to reflection from interfaces between said films. Said individual data sets can be used in simultaneous regression onto a mathematical model.

In any of the foregoing methods, an additional step can be to position a small aperture in front of the detector, optical fiber or detector element so that substantially only electromagnetic radiation reflected from the frontside, or an interface, or substantially only electromagnetic radiation reflected from the backside enters thereinto, with only minimal influence from backside or frontside reflected electromagnetic radiation, respectively. Said aperture can be movable with a movable detector or optical fiber, or one or more apertures can be positioned, in place, with respect to fixed position elements of a multi-detector element detector.

The present invention will be better understood by reference to the Detailed description Section of this Specification, in conjunction with the Drawings.

DETAILED DESCRIPTION

Figure 1:
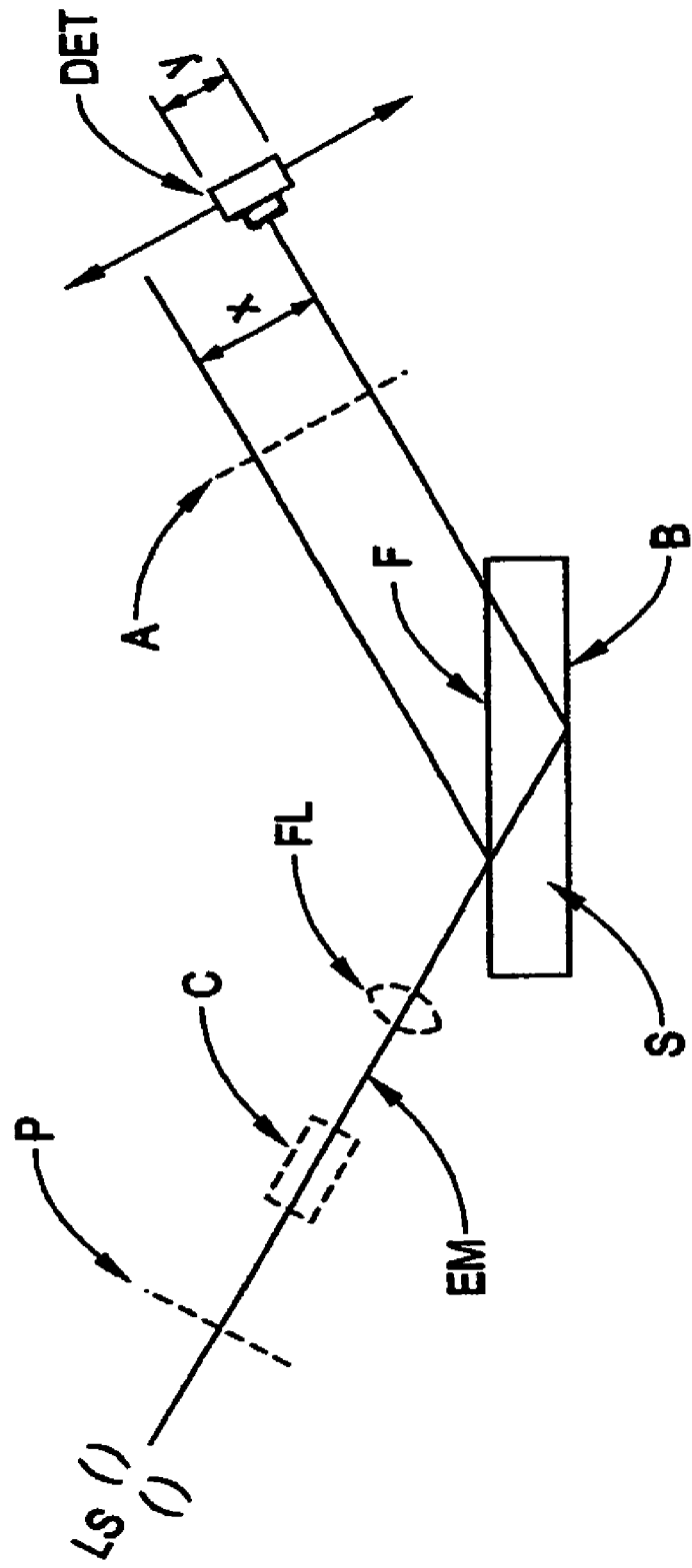
FIG. 1 shows a present invention system configuration including a detector (DET).

FIG. 1 shows a present invention system configuration. Shown are a Source of Electromagnetic Radiation (LS), a Sample (S) having Surface (F) and a Back (B) side, and a Detector (DET); said Source (LS), Sample (S) and Detector (DET) being oriented such that Electromagnetic Radiation (EM) from said Source (S) is directed at said Sample (S) at an oblique angle, reflects therefrom and enters said Detector (DET). Note that said Detector (DET) is of a Small Dimension (Y) as compared to the Spread (X) between sample Surface (F) and sample Backside (B) Reflections at its location. Also note that said Detector (DET) is mounted to allow movement into Electromagnetic Radiation Reflected from the Frontside (F) or Backside (B) of said Sample (S). It is mentioned that the distance "X" is increased by directing electromagnetic beam from source (LS) incident on the sample (S) via a Focusing lens (FL), and that an increased, (ie. rotated from a normal to the sample surface oriented), angle-of-incidence can also increase "X".

The detector (DET) in FIG. 1 is shown with an attachment which first intercepts a beam of electromagnetic radiation. This can be considered to be an aperture which serves to enable better identifying a peak location (see P1 or P2 in FIG. 4), by, for instance, reducing frontside reflection effects on peak (P2) and backside reflection effects on peak (P1). It is noted that a detector to intercept backside transmission data can also be present.

Figure 2:
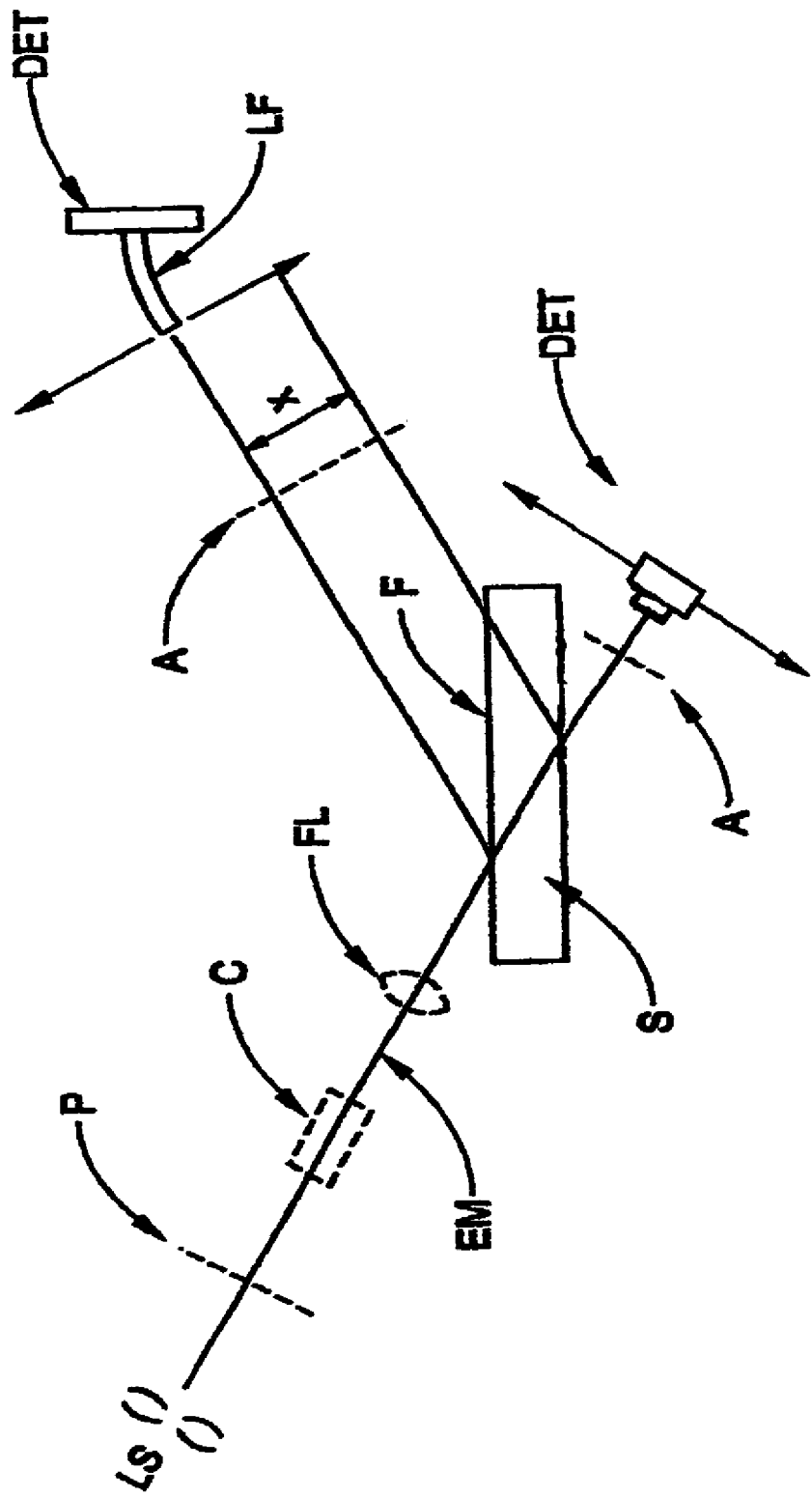
FIG. 2 shows a system like that in FIG. 1, with the detector (DET) replaced by the very small end of an optical fiber (LF), and also indicates a detector for intercepting a transmitted beam.

FIG. 2 shows a system like that in FIG. 1, except that the reflection monitoring Detector (DET) is replaced by the very small end of an Optical Fiber (LF), which is shown positioned to receive the reflection from the Front Surface (F) of the Sample (S). FIG. 2 also demonstrates that electromagnetic radiation transmitted through the backside can also be acquired. A small detector is shown but a light fiber, (eg. the same light fiber (LF) and detector (DET) shown could be utilized. It is to be understood that the configuration of FIGS. 1 and 3 can also include means to detect backside transmission data.

Said System (S) can further comprise at least one selection from the group consisting of:
 a Polarizer (P) means between said Source (LS) and Sample (S);
 an Analyzer (A) means between said Sample (S) and Detector (DET);
 a Compensator (C) between said Source (LS) and Detector (DET); and
 at least one Focusing Lens (FL);

wherein said system is an ellipsometer or polarimeter.

Note, it is to be understood that as used in the Claims, the terminology "detector" is to be interpreted to include a small detector per se. or a light fiber detector combination. Further, where physically possible, (eg. as FIGS. 1 and 2 could allow), the same detector can be used to sequentially obtain frontside and backside reflection, and backside transmission data. It is noted that the Detector Elements (DE) can be the ends of a plurality of Light Fibers (LF).

Figure 3:
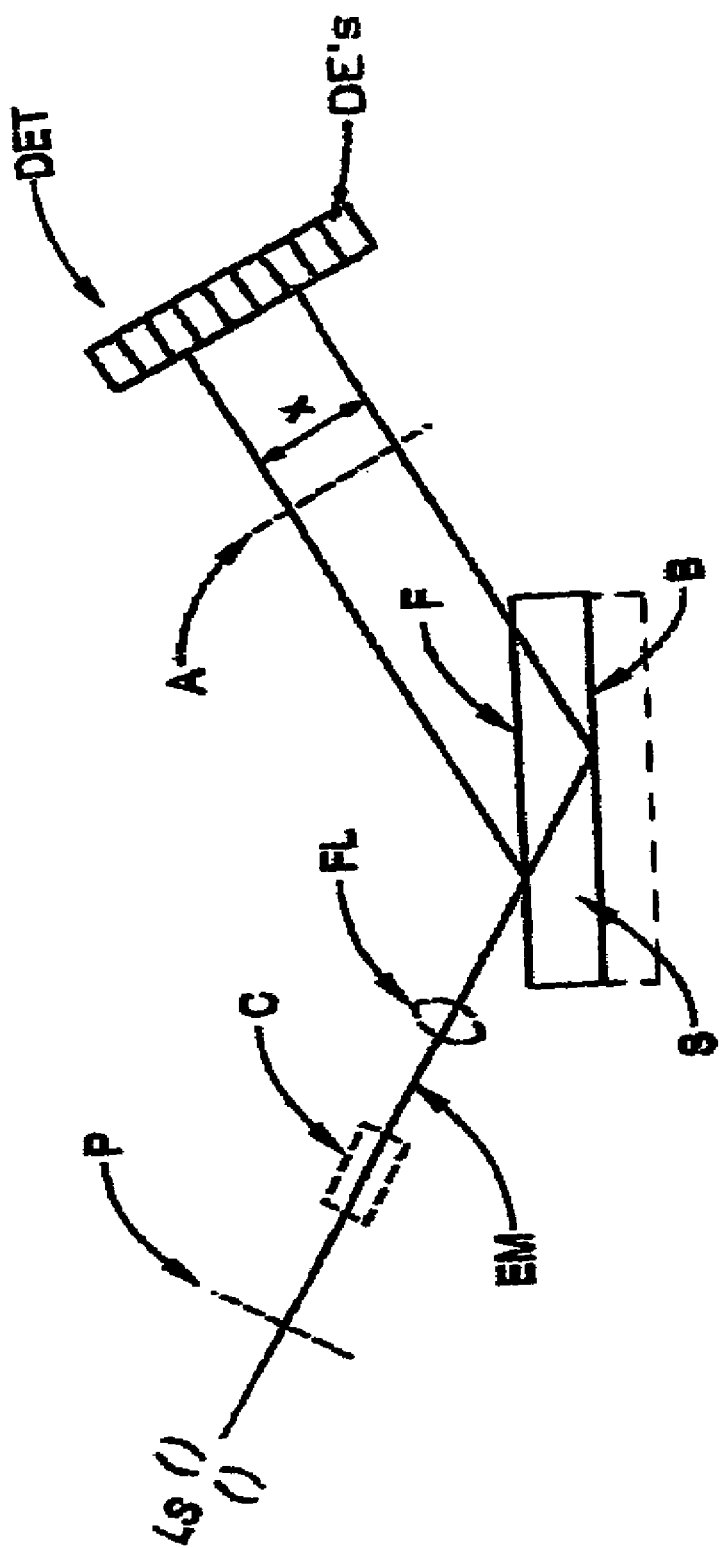
FIG. 3 shows a system like that in FIG. 1, with the detector (DET) comprising a plurality of small detector elements (DE's).

FIG. 3 shows a system (S) which is sequentially comprised of a source (LS) of electromagnetic radiation, a sample (S) having Frontside (F) and a Backside (B), and a detector (DET) which comprises a plurality of detector elements (DE's). Said source (LS), sample (S) and detector (DET) are oriented such that electromagnetic radiation from said source is directed at said sample at an oblique angle, reflects therefrom and enters said detector (DET), said detector elements (DE's) being of a small dimension as compared to the spread between sample frontside (F) and sample backside (B) reflections at its location, such that selective monitoring of specific detector elements (DE's) allows the monitoring of reflections from the frontside (F) and backside (B) independently. While the system is not unique, it can be applied in what is believed to be a new and novel method involving separate analysis of frontside and backside reflections. For instance, reflections from the frontside (F) provide information primarily about the surface region of the sample, while reflections from the back (B) of the sample (S) provide information about the bulk of the sample (S). The method can also utilize data acquired by monitoring backside transmitted electromagnetic radiation.

Figure 4:
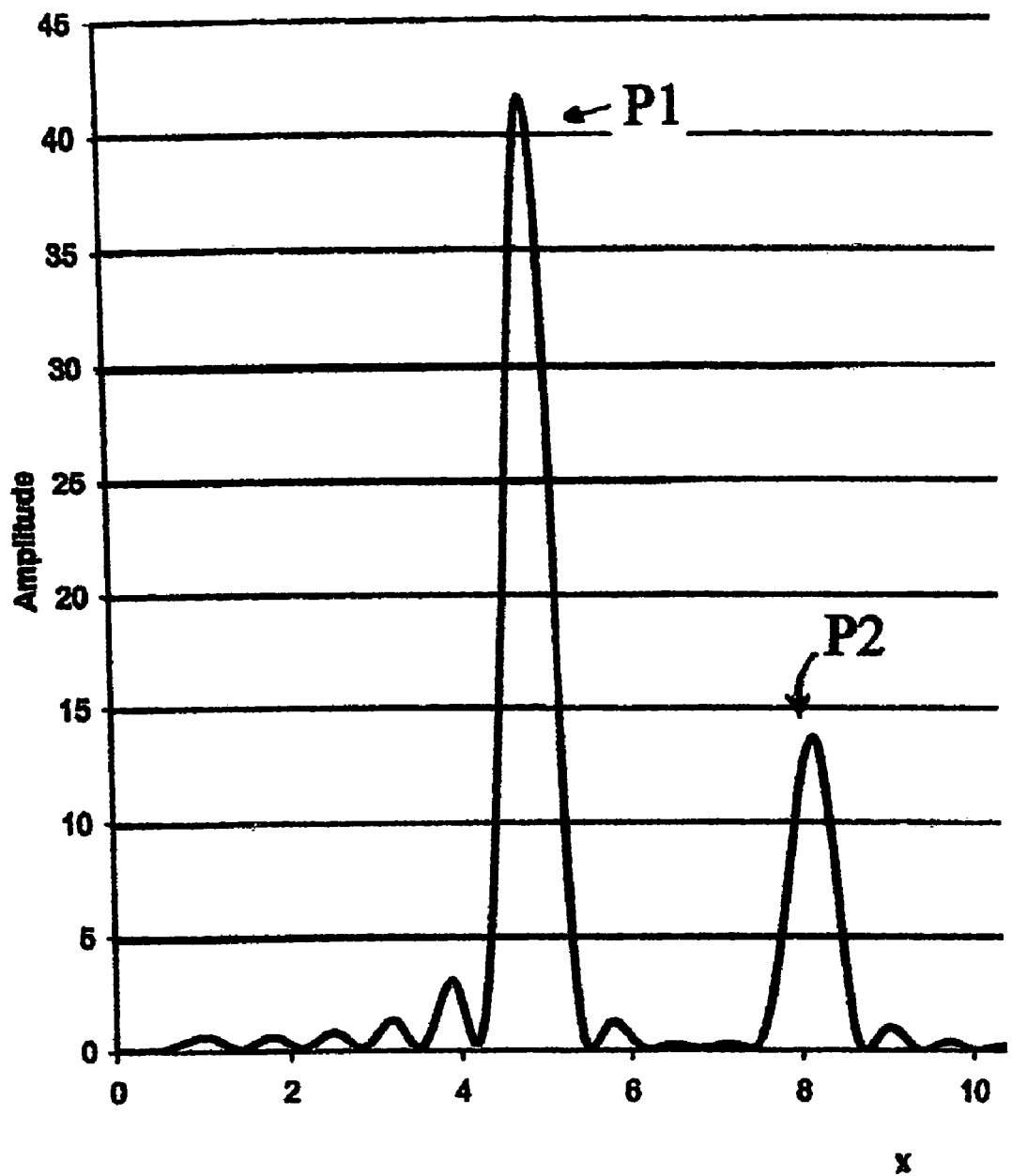
FIG. 4 shows a plot of amplitude vs. "X".

FIG. 4 shows a plot of amplitude vs. "X", as identified in FIGS. 1-3. Peaks P1 and P2 correspond to front and backside reflections, and are presented in terms of arbitrary units. As regards FIGS. 1 and 2 the peaks P1 and P2 will be obtained as the detector (DET) of optical fiber (LP) is moved so as to intercept the frontside and backside reflections, and as regards FIG. 3, the peaks correspond to output from the detector elements (DE) which intercept the front and backside reflections. Peak P2 is shown as less intense, by a demonstrative arbitrary amount, as the electromagnetic radiation in a backside reflection must transverse the thickness of the substrate (S) twice, (once going in and once going back out), and therefore can be expected to be somewhat attenuated as compared to electromagnetic radiation reflecting from the front surface. Data corresponding to the front and backside reflections are acquired substantially where a peak is found. Peak (P2) could also represent backside transmission data.

It is mentioned that FIGS. 1-3 are demonstrative only of important aspects of the present invention. Physically real samples would, of course, bend the electromagnetic beams entering into the sample, and exiting beams would also be re-directed based on Snell's law. The important aspect of the present invention demonstrated by the Drawings is that reflected frontside and backside, and backside transmitted electromagnetic radiation can be individually monitored and multiple data sets can be developed based on what electromagnetic radiation is monitored. These different data sets can be individually utilized in analysis procedures, or a plurality of said data sets can be simultaneously utilized. I-t is also noted that the terminology "frontside reflection" is to be interpreted to include per se. surface reflections from the actual surface of the sample, or said "frontside" reflections can be from interfaces between films on a substrate (not shown). Where there are a plurality of such reflections any thereof can be independently monitored to provide an individual data set, and is included in the terminology "frontside reflection". Further, where a frontside reflection is identified, (be it from the surface of the sample per se. or from an interface, a reflection from an interface located deeper in the sample can be considered a "backside reflection". That is, a frontside reflection can be from the surface of the sample or from an interface between two layers, or from a layer and the sample substrate; and a backside reflection can be from the back surface of the sample, or from an interface between two layers, or a layer and the sample substrate, which originates deeper in the sample as measured from the sample front surface, than is a frontside reflection. As an example, the sample (S) in FIG. 1 or 3, (see dashed lines in FIG. 3 indicating the optional presence of a substrate), can be interpreted to be a film layer atop a substrate, with the Frontside (F) being the surface per se., and with the Backside (B) being an interface between said film layer and the sample substrate. And said layer could be buried under additional Frontside layers. A plurality of frontside and backside data sets which originate from interfaces between a plurality of film layers on a sample can be individually analyzed, or simultaneously applied in a regression procedure, for instance. Further, transmission data from the backside of the sample can also be analyzed Independently or simultaneously with various reflection data sets.

The methodology of use is presented in the Disclosure of the Invention Section of this Specification.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of selectively monitoring frontside or backside reflections from a sample, comprising the steps of:
   a) providing a system which is sequentially comprised of a source of electromagnetic radiation, a sample having a frontside and a backside, and a detector; said source, sample and detector being oriented such that electromagnetic radiation from said source is directed at said sample at an oblique angle, reflects therefrom and enters said detector, said detector being of a small dimension as compared to the spread between sample frontside and sample backside reflections at the location thereof, said detector being mounted to allow movement into electromagnetic radiation reflected from the frontside or backside;
   b) causing a beam of electromagnetic radiation to reflect from said sample; and
   c) moving said detector into electromagnetic radiation reflected from the sample frontside or from the sample backside and obtaining data and acquiring data.

2. A method as in claim 1 in which the step of providing a system further comprises providing at least one selection from the group consisting of:
   a polarizer means between said source and sample;
   an analyzer means between said sample and detector;
   a compensator between said source and detector; and
   at least one focusing lens positioned such that electromagnetic radiation from said source is directed at said sample at an oblique angle.

3. A system which is sequentially comprised of a source of electromagnetic radiation, a sample having a frontside and a backside, and at least one detector; said source, sample and at least one detector being oriented such that electromagnetic radiation from said source is directed at said sample at an oblique angle, reflects therefrom and/or is transmitted therethrough and enters said at least one detector, said at least one detector being of a small dimension as compared to the spread between sample frontside and sample backside reflections at the location thereof, said at least one detector being mounted to allow movement into electromagnetic radiation reflected from the frontside or backside or transmitted through said backside.

4. A system as in claim 3 in which said system further comprises providing at least one selection from the group consisting of:
   a polarizer means between said source and sample;
   an analyzer means between said sample and detector;
   a compensator between said source and detector; and
   at least one focusing lens positioned such that electromagnetic radiation from said source is directed at said sample at an oblique angle.

5. A method of selectively monitoring frontside or backside reflections from a sample, or transmission therethrough comprising the steps of:
   a) providing a system which is sequentially comprised of a source of electromagnetic radiation, a sample having a frontside and a backside, and at least one detector; said source, sample and at least one detector being oriented such that electromagnetic radiation from said source is directed at said sample at an oblique angle, reflects therefrom and/or is transmitted therethrough and enters said at least one detector, said at least one detector being of a small dimension as compared to the spread between sample frontside and sample backside reflections at the location thereof, said at least one detector being mounted to allow movement into electromagnetic radiation reflected from the frontside or backside or transmitted through said backside;

b) causing a beam of electromagnetic radiation to reflect from said sample; and c) moving said detector into electromagnetic radiation reflected from the sample frontside or from the sample backside or which is transmitted through said sample backside and obtaining data.

6. A method as in claim 5 in which the step of providing a system further comprises providing at least one selection from the group consisting of:

a polarizer means between said source and sample;

an analyzer means between said sample and detector;

a compensator between said source and detector; and at least one focusing lens positioned such that electromagnetic radiation from said source is directed at said sample at an oblique angle.

7. A method as in claim 1 in which analysis of the reflections from the frontside and backside of the sample are analyzed separately with the reflection from the frontside providing information about the surface region of the sample and the reflection from the backside thereof providing information about the bulk of the sample.

8. A method as in claim 1 in which the system provided is a reflectometer or spectrophotometer.

9. A system as in claim 3, which comprises a reflectometer or spectrophotometer.

10. A method as in claim 5 in which the system provided is a reflectometer or spectrophotometer.

11. A method as in claim 2 in which the system provided is an ellipsometer or polarimeter.

12. A system as in claim 4, which comprises an ellipsometer or polarimeter.

13. A method as in claim 6 in which the system provided is an ellipsometer or polarimeter.

14. A method of pursuing uncorrelated determination of refractive index and thickness of a sample comprising:

practicing steps a and a' sequentially or simultaneously in either order:

a) providing a system which is sequentially comprised of a source of electromagnetic radiation, a sample having frontside and a backside, and at least one detector that allows selective monitoring at least two selections from the group consisting of:

reflection from the frontside;
reflection from the backside; and
transmission through the backside;

independently, said detector(s) being selected from the group consisting of:

comprising a plurality of substantially fixed location detector elements;
comprising a movable detector element; and
comprising a detector element accessed by a movable optical fiber;

said source, sample and detector being oriented such that electromagnetic radiation from said source is directed at said sample at an oblique angle;

a') providing a mathematical model of said sample;

b) causing a beam of electromagnetic radiation to impinge onto said sample at an oblique angle of incidence; and c) independently monitoring at least two selections form the group consisting of:

reflection from the frontside;
reflection from the backside; and
transmission through the backside;

d) simultaneously regressing at least two monitored data sets obtained in step c onto said mathematical model provided in step a'.

15. A method as in claim 14 in which the step of providing a system further comprises providing at least one selection from the group consisting of:

a polarizer means between said source and sample;
an analyzer means between said sample and detector;
a compensator between said source and detector; and
at least one focusing lens positioned such that electromagnetic radiation from said source is directed at said sample at an oblique angle.

16. A method as in claim 14 which further comprises flipping the sample over so that the sample backside becomes the frontside and the sample frontside becomes the backside, and obtaining data by repeating step c, and further including said additional data in the simultaneous regression onto the mathematical model in step d.

17. A system as in claim 14, which the system provided is a reflectometer or spectrophotometer.

18. A system as in claim 15, which comprises an ellipsometer or polarimeter.

19. A method as in claim 14, in which the sample comprises a substrate.

20. A method as in claim 14, in which the sample comprises a substrate and at least one film layer on at least one of the front and backsides thereof.

* * * * *